United States Patent [19]

Savage et al.

[11] Patent Number: Plant 7,456

[45] Date of Patent: Feb. 26, 1991

[54] MAGNOLIA TREE NAMED BUTTERFLIES

[75] Inventors: Philip G. Savage; Roy G. Klehm, both of S. Barrington, Ill.

[73] Assignees: Justine B. Savage; Sarah L. Klehm, both of South Barrington, Ill.

[21] Appl. No.: 433,960

[22] Filed: Nov. 9, 1989

[51] Int. Cl.[5] ..... A01H 5/00

[52] U.S. Cl. ..... Plt./51

[58] Field of Search ..... Plt./51

[56] References Cited

U.S. PATENT DOCUMENTS

P.P. 4,145 11/1977 Specht ..... Plt. 51

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A magnolia tree named Butterflies particularly characterized by its deep rich yellow flower color, thick display of cup-shaped flowers which are carried upright and are non-fading, start of vegetative growth only after tepals have fallen, pyramidal growing habit with single trunk and symmetrical branches, abundant dark green foliage, and hardiness to climate conditions in zones 5–9.

2 Drawing Sheets

The present invention comprises a new and distinct cultivar of magnolia tree, a hybrid of *M. acuminata* and *M. denudata,* and hereinafter referred to by the cultivar name Butterflies.

The new cultivar is the result of a breeding program carried out co-inventor Philip J. Savage in Bloomfield Hills, Mich. With the aim of producing a superior ornamental magnolia cultivar, many different clones of *M. acuminata* were hand pollinated with pollen from several clones of *M. denudata.* A great many seedlings were grown to flowering age and the best individual of all the crosses was selected for its deep yellow flower color which does not fade, late vegetative growth, pleasing compact pyramidal form bearing attractive dark green foliage, and its unusual hardiness to cold and heat.

Asexual reproduction by co-inventor Roy G. Klehm in South Barrington, Ill. in the forms of softwood cuttings, chip budding and side grafting has demonstrated that the combination of characteristics as herein disclosed for the new cultivar are firmly fixed and retained through successive generations of asexual reproduction.

Butterflies has not been observed under all possible environmental conditions. The phenotype may vary significantly with variations in environment such as temperature, light intensity and day length. The following observations, measurements and comparisons describe trees grown in Michigan, Wisconsin and Illinois under conditions which approximate those generally used in commercial practice.

The following traits have been repeatedly observed and are determined to be basic characteristics of Butterflies which in combination distinguish this magnolia tree as a new and distinct cultivar:

1. The flowers display a deeper, richer and purer yellow color than any other cultivar known to date.

2. Flowers are carried upright, like a Darwin tulip, and are thickly disposed throughout the tree.

3. Leaf buds do not open, or vegetative growth start, until tepals, without fading, have fallen.

4. Flowers carry from ten to sixteen tepals and maintain an attractive cup shape throughout.

5. The tree develops a neat pyramidal habit, with a straight, single trunk and symmetrical branches.

6. Foliage is generous and dark green, with the underside of the leaves being a few shades lighter.

7. The bark of the trunk and large branches is a medium gray, with twigs darker and browner.

8. Butterflies is hardy from U.S. Department of Agricultural (U.S.D.A.) zone 5 to zone 9, and all zones between, surviving −29° F.

Of the many commercial magnolia trees known to the inventor, the most similar in comparison to Butterflies is the magnolia hybrid Elizabeth. In comparison to Elizabeth, Butterflies has flowers of a deeper yellow color, with a larger number of petals, and vegetative buds that do not open until the non-fading flowers have matured and shattered cleanly off the twigs.

The accompanying color photographic drawings show typical characteristics of Butterflies, with colors being as true as possible with illustrations of this type.

Sheet 1 comprises a view of a typical tree of Butterflies in bloom.

Sheet 2 comprises a closeup of a single flower of Butterflies.

In the following description, color references are made to the Royal Horticultural Society Colour Chart (R.H.S.). The color values were determined between 12:00 noon and 1:00 p.m. on May 8, 1988 under sunny conditions at 2150 Woodward Avenue, Bloomfield Hills, Mich.

Origin: Magnolia hybrid Butterflies is the best of twenty seedlings from hand pollination of.

Parentage:

*Seed parent.*—*M. acuminata* (north Ohio origin).

*Pollen parent.*—A *M. denudata* seedling with exceptionally rich, cream-colored buds and flowers (Japanese origin).

Classification:

*Botanical.*—Both parents are species of sub-genus Yulania.

*Commercial.*—Magnolia hybrid Butterflies.

Propagation: Softwood cuttings and "chip" budding.

Trunk: 21 cm. diameter at one meter above root crown.

Branches: Symmetrical, spreading to 3.5 m. at 14 years old.

Height: 5 m. at 14 years from seed.

Growth habit: Symmetrical, oval pyramid, single leader.

Fruit bearing habit: Rarely sets open-pollinated seed.

Spreading habit: 3.5 m. at 1 m. above root crown.

Cold hardiness: U.S.D.A. Zone 5; bloomed after −29° in previous winter.

Foliage:

*Size of leaf.*—15 cm. × 10 cm.

*Shape of leaf.*—Oblong/elliptic; cuneate base; cuspidate tip.

*Margin.*—Entire.

*Texture.*—Firm and flat, but not coriaceous.

*Color.*—Upper surface: Green 137A. Lower surface: Green 137B.

*Petiole.*—1.5 cm. long, strong.

*Hair.*—Upper surface: Nearly glabrous. Lower surface: Sparse silver hairs on veins.

Inflorescence:

*Size.*—7 cm. across top of "cup".

*Shape.*—Upright "tulip"; tepals open to 45° from vertical.

*Buds.*—Thickly pubescent, with glossy, silver hairs.

*Blooming habit.*—Precocious, all flowers opening at once.

*Floriferousness.*—Flowers abundant over entire tree.

*Petals.*—Number: Ten to sixteen. Shape: Broadly spoon shaped; overlapping. Length: Seven to eight cm. Width: Two and one half to four cm. Color: Outer surface, yellow 3B. Inner surface, yellow 3C. Texture: Smooth, durable, heavy substance. Fragrance: Light scent of lemon oil. Retention: Seven to nine days; shatter cleanly. Reproductive parts: Gynoecium small, light green, stamens and anthers raspberry pink.

*Fruit.*—Seldom produced by insect pollination; reddish-green when mature (carpophore).

*Seed.*—Outer testa orange red; inner coat shiny black with small cusp. Similar to *M. denudata.*

I claim:

1. A new and distinct cultivar of magnolia tree named Butterflies, as illustrated and described.

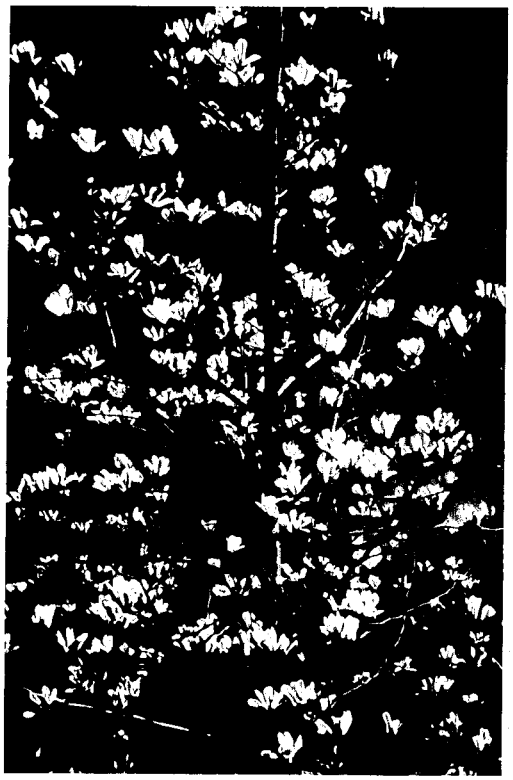

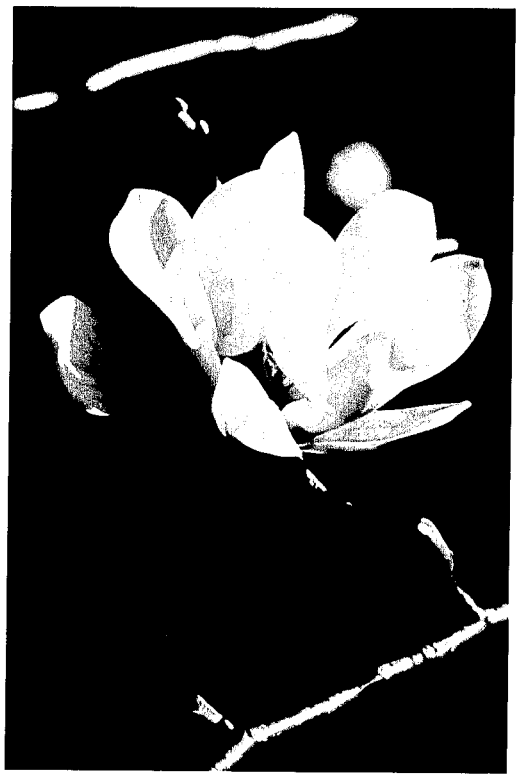

* * * * *